(12) United States Patent
Gross

(10) Patent No.: US 9,186,504 B2
(45) Date of Patent: Nov. 17, 2015

(54) SLEEP APNEA TREATMENT

(71) Applicant: RAINBOW MEDICAL LTD., Herzliya (IL)

(72) Inventor: Yossi Gross, Moshav Mazor (IL)

(73) Assignee: RAINBOW MEDICAL LTD, Herzliya (IL)

( * ) Notice: Subject to any disclaimer, the term of this patent is extended or adjusted under 35 U.S.C. 154(b) by 0 days.

(21) Appl. No.: 14/559,907

(22) Filed: Dec. 3, 2014

(65) Prior Publication Data

US 2015/0148861 A1 May 28, 2015

Related U.S. Application Data

(63) Continuation-in-part of application No. 13/885,360, filed as application No. PCT/IL2011/000870 on Nov. 10, 2011, now abandoned, which is a continuation of application No. 12/946,246, filed on Nov. 15, 2010, now abandoned.

(51) Int. Cl.
*A61N 1/00* (2006.01)
*A61N 1/36* (2006.01)
(Continued)

(52) U.S. Cl.
CPC .............. *A61N 1/3601* (2013.01); *A61B 19/52* (2013.01); *A61N 1/3787* (2013.01); *A61N 1/37223* (2013.01)

(58) Field of Classification Search
CPC .............. A61N 1/3601; A61N 1/3611; A61N 1/36135; A61N 1/36139; A61N 1/0548; A61B 5/0013; A61B 5/0002; A61B 5/11; A61B 5/1114; A61B 5/113
See application file for complete search history.

(56) References Cited

U.S. PATENT DOCUMENTS 3,411,507 A 11/1968 Wingrove
4,019,518 A 4/1977 Maurer et al.
(Continued)

FOREIGN PATENT DOCUMENTS

CN 102973244 3/2013
EP 0688577 12/1995
(Continued)

OTHER PUBLICATIONS

De Balthasar, G. Cosendai, M. Hansen, D. Canfield, L. Chu, R. Davis, and J. Schulman, "Attachment of leads to RF-BION® microstimulators." Jul. 2005.
(Continued)

*Primary Examiner* — Michael Kahelin
*Assistant Examiner* — Mallika D Fairchild
(74) *Attorney, Agent, or Firm* — Symbus Law Group, LLC; Clifford D. Hyra

(57) ABSTRACT

Apparatus and methods are described, including apparatus for treating a subject for obstructive sleep apnea (OSA). The apparatus includes an implant, an imaging device, and a control unit. In response to a set of training images received from the imaging device, the control unit learns an association between a position of a head of the subject and OSA of the subject. In response to the association, the control unit establishes, for an OSA-related parameter, at least two distinct thresholds corresponding to respective different head positions. Subsequently, at a second time, the control unit selects a threshold that corresponds to the position of the subject's head, and if the value of the OSA-related parameter passes the selected threshold, treats the subject for OSA by driving the implant to apply current to an anatomical site of the subject. Other applications are also described.

12 Claims, 4 Drawing Sheets

(51) Int. Cl.

| A61N 1/372 | (2006.01) |
| --- | --- |
| A61B 19/00 | (2006.01) |
| A61N 1/378 | (2006.01) |

(56) References Cited

U.S. PATENT DOCUMENTS

| | | |
| --- | --- | --- |
| 4,338,945 A | 7/1982 | Kosugi et al. |
| 4,350,166 A | 9/1982 | Mobarry |
| 4,392,496 A | 7/1983 | Stanton |
| 4,535,785 A | 8/1985 | van den Honert et al. |
| 4,559,948 A | 12/1985 | Liss et al. |
| 4,573,481 A | 3/1986 | Bullara |
| 4,585,005 A | 4/1986 | Lue et al. |
| 4,602,624 A | 7/1986 | Naples et al. |
| 4,608,985 A | 9/1986 | Crish et al. |
| 4,628,942 A | 12/1986 | Sweeney et al. |
| 4,632,116 A | 12/1986 | Rosen et al. |
| 4,649,936 A | 3/1987 | Ungar |
| 4,663,102 A | 5/1987 | Brenman et al. |
| 4,739,764 A | 4/1988 | Lue et al. |
| 4,867,164 A | 9/1989 | Zabara |
| 4,926,865 A | 5/1990 | Oman |
| 4,962,751 A | 10/1990 | Krauter |
| 5,025,807 A | 6/1991 | Zabara |
| 5,069,680 A | 12/1991 | Grandjean |
| 5,178,161 A | 1/1993 | Kovacs |
| 5,188,104 A | 2/1993 | Wernicke et al. |
| 5,199,428 A | 4/1993 | Obel et al. |
| 5,199,430 A | 4/1993 | Fang et al. |
| 5,203,326 A | 4/1993 | Collins |
| 5,205,285 A | 4/1993 | Baker, Jr. |
| 5,215,086 A | 6/1993 | Terry, Jr. et al. |
| 5,263,480 A | 11/1993 | Wernicke |
| 5,282,468 A | 2/1994 | Klepinski |
| 5,292,344 A | 3/1994 | Douglas |
| 5,299,569 A | 4/1994 | Wernicke et al. |
| 5,314,495 A | 5/1994 | Kovacs |
| 5,330,507 A | 7/1994 | Schwartz |
| 5,335,657 A | 8/1994 | Terry, Jr. et al. |
| 5,423,872 A | 6/1995 | Cigaina |
| 5,439,938 A | 8/1995 | Snyder et al. |
| 5,454,840 A | 10/1995 | Krakovsky et al. |
| 5,505,201 A | 4/1996 | Grill, Jr. et al. |
| 5,540,730 A | 7/1996 | Terry, Jr. et al. |
| 5,540,733 A | 7/1996 | Testerman et al. |
| 5,540,734 A | 7/1996 | Zabara |
| 5,549,655 A | 8/1996 | Erickson |
| 5,571,150 A | 11/1996 | Wernicke et al. |
| 5,591,216 A | 1/1997 | Testerman et al. |
| 5,634,462 A | 6/1997 | Tyler et al. |
| 5,690,681 A | 11/1997 | Geddes et al. |
| 5,690,691 A | 11/1997 | Chen et al. |
| 5,700,282 A | 12/1997 | Zabara |
| 5,704,367 A | 1/1998 | Ishikawa et al. |
| 5,707,400 A | 1/1998 | Terry, Jr. et al. |
| 5,711,316 A | 1/1998 | Elsberry et al. |
| 5,716,385 A | 2/1998 | Mittal et al. |
| 5,755,750 A | 5/1998 | Petruska et al. |
| 5,776,171 A | 7/1998 | Peckham et al. |
| 5,814,089 A | 9/1998 | Stokes et al. |
| 5,824,027 A | 10/1998 | Hoffer et al. |
| 5,832,932 A | 11/1998 | Elsberry et al. |
| 5,833,709 A | 11/1998 | Rise et al. |
| 5,836,994 A | 11/1998 | Bourgeois |
| 5,916,239 A | 6/1999 | Geddes et al. |
| 5,938,584 A | 8/1999 | Ardito et al. |
| 5,944,680 A | 8/1999 | Christopherson et al. |
| 5,954,758 A | 9/1999 | Peckham et al. |
| 6,026,326 A | 2/2000 | Bardy |
| 6,026,328 A | 2/2000 | Peckham et al. |
| 6,058,331 A | 5/2000 | King |
| 6,066,163 A | 5/2000 | John |
| 6,083,249 A | 7/2000 | Familoni |
| 6,086,525 A | 7/2000 | Davey et al. |
| 6,091,977 A | 7/2000 | Tarjan et al. |
| 6,091,992 A | 7/2000 | Bourgeois et al. |
| 6,094,598 A | 7/2000 | Elsberry et al. |
| 6,097,984 A | 8/2000 | Douglas |
| 6,104,955 A | 8/2000 | Bourgeois |
| 6,104,960 A | 8/2000 | Duysens et al. |
| 6,119,516 A | 9/2000 | Hock |
| 6,146,335 A | 11/2000 | Gozani |
| 6,148,232 A | 11/2000 | Avrahami |
| 6,169,924 B1 | 1/2001 | Meloy et al. |
| 6,205,359 B1 | 3/2001 | Boveja |
| 6,212,435 B1 | 4/2001 | Lattner et al. |
| 6,214,032 B1 | 4/2001 | Loeb et al. |
| 6,230,061 B1 | 5/2001 | Hartung |
| 6,240,316 B1 | 5/2001 | Richmond et al. |
| 6,266,564 B1 | 7/2001 | Hill et al. |
| 6,272,383 B1 | 8/2001 | Grey et al. |
| 6,292,703 B1 | 9/2001 | Meier et al. |
| 6,319,241 B1 | 11/2001 | King et al. |
| 6,332,089 B1 | 12/2001 | Acker et al. |
| 6,341,236 B1 | 1/2002 | Osorio et al. |
| 6,345,202 B2 | 2/2002 | Richmond et al. |
| 6,356,784 B1 | 3/2002 | Lozano et al. |
| 6,356,788 B2 | 3/2002 | Boveja |
| 6,366,813 B1 | 4/2002 | DiLorenzo |
| 6,405,079 B1 | 6/2002 | Ansarinia |
| 6,445,953 B1 | 9/2002 | Bulkes et al. |
| 6,449,507 B1 | 9/2002 | Hill et al. |
| 6,463,328 B1 | 10/2002 | John |
| 6,473,644 B1 | 10/2002 | Terry, Jr. et al. |
| 6,600,954 B2 | 7/2003 | Cohen et al. |
| 6,600,956 B2 | 7/2003 | Maschino et al. |
| 6,610,713 B2 | 8/2003 | Tracey |
| 6,618,627 B2 | 9/2003 | Lattner et al. |
| 6,641,542 B2 | 11/2003 | Cho et al. |
| 6,682,480 B1 | 1/2004 | Habib et al. |
| 6,735,474 B1 | 5/2004 | Loeb et al. |
| 6,770,022 B2 | 8/2004 | Mechlenburg et al. |
| 6,829,508 B2 | 12/2004 | Schulman et al. |
| 6,839,594 B2 | 1/2005 | Cohen et al. |
| 6,892,098 B2 | 5/2005 | Ayal et al. |
| 6,909,917 B2 | 6/2005 | Woods et al. |
| 7,025,730 B2 | 4/2006 | Cho et al. |
| 7,027,860 B2 | 4/2006 | Bruninga et al. |
| 7,177,698 B2 | 2/2007 | Klosterman et al. |
| 7,228,178 B2 | 6/2007 | Carroll et al. |
| 7,277,749 B2 | 10/2007 | Gordon et al. |
| 7,324,852 B2 | 1/2008 | Barolat et al. |
| 7,324,853 B2 | 1/2008 | Ayal et al. |
| 7,532,932 B2 | 5/2009 | Denker et al. |
| 7,536,226 B2 | 5/2009 | Williams et al. |
| 7,628,750 B2 | 12/2009 | Cohen et al. |
| 7,630,771 B2 | 12/2009 | Cauller |
| 7,660,632 B2 | 2/2010 | Kirby et al. |
| 7,680,538 B2 | 3/2010 | Durand et al. |
| 7,711,438 B2 | 5/2010 | Lattner et al. |
| 7,797,050 B2 | 9/2010 | Libbus et al. |
| 7,848,818 B2 | 12/2010 | Barolat et al. |
| 7,917,226 B2 | 3/2011 | Nghiem et al. |
| 7,974,706 B2 | 7/2011 | Moffitt et al. |
| 7,996,089 B2 | 8/2011 | Haugland et al. |
| 7,996,092 B2 | 8/2011 | Mrva et al. |
| 8,019,443 B2 | 9/2011 | Schleicher et al. |
| 8,131,377 B2 | 3/2012 | Shi et al. |
| 8,185,207 B2 | 5/2012 | Molnar et al. |
| 8,634,927 B2 | 1/2014 | Olson et al. |
| 8,679,034 B2 | 3/2014 | Halperin et al. |
| 8,786,698 B2 | 7/2014 | Chen et al. |
| 2002/0099419 A1 | 7/2002 | Cohen et al. |
| 2003/0040774 A1 | 2/2003 | Terry, Jr. et al. |
| 2003/0100933 A1 | 5/2003 | Ayal et al. |
| 2003/0176898 A1 | 9/2003 | Gross et al. |
| 2004/0010303 A1 | 1/2004 | Bolea et al. |
| 2004/0015205 A1 | 1/2004 | Whitehurst et al. |
| 2004/0019368 A1* | 1/2004 | Lattner et al. .............. 607/42 |
| 2004/0048795 A1 | 3/2004 | Ivanova et al. |
| 2004/0073270 A1 | 4/2004 | Firlik et al. |
| 2004/0254624 A1 | 12/2004 | Johnson |
| 2005/0085868 A1 | 4/2005 | Tehrani et al. |
| 2005/0107722 A1* | 5/2005 | Ozaki et al. .............. 600/587 |

(56) References Cited

U.S. PATENT DOCUMENTS

| | | |
|---|---|---|
| 2005/0143789 A1 | 6/2005 | Whitehurst et al. |
| 2005/0165457 A1 | 7/2005 | Benser et al. |
| 2006/0100668 A1 | 5/2006 | Ben-David et al. |
| 2006/0155345 A1 | 7/2006 | Williams et al. |
| 2006/0271137 A1 | 11/2006 | Stanton-Hicks |
| 2007/0067000 A1 | 3/2007 | Strother et al. |
| 2007/0173893 A1 | 7/2007 | Pitts |
| 2007/0191904 A1 | 8/2007 | Libbus et al. |
| 2008/0027513 A1 | 1/2008 | Carbunaru |
| 2008/0039915 A1 | 2/2008 | Van Den Biggelaar et al. |
| 2008/0103407 A1 | 5/2008 | Bolea et al. |
| 2008/0103572 A1 | 5/2008 | Gerber |
| 2009/0012590 A1 | 1/2009 | Inman et al. |
| 2009/0048642 A1 | 2/2009 | Goroszeniuk |
| 2009/0112285 A1 | 4/2009 | Cahan et al. |
| 2009/0281594 A1 | 11/2009 | King et al. |
| 2010/0121405 A1 | 5/2010 | Ternes et al. |
| 2010/0125310 A1 | 5/2010 | Wilson et al. |
| 2010/0198298 A1 | 8/2010 | Glukhovsky et al. |
| 2010/0241195 A1 | 9/2010 | Meadows et al. |
| 2010/0312320 A1 | 12/2010 | Faltys et al. |
| 2011/0046696 A1 | 2/2011 | Barolat et al. |
| 2011/0093036 A1 | 4/2011 | Mashiach |
| 2011/0137365 A1 | 6/2011 | Ben-Ezra et al. |
| 2011/0152965 A1 | 6/2011 | Mashiach et al. |
| 2011/0160798 A1 | 6/2011 | Ackermann, Jr. et al. |
| 2011/0208271 A1 | 8/2011 | Dobak |
| 2011/0224744 A1 | 9/2011 | Moffitt et al. |
| 2011/0282412 A1 | 11/2011 | Glukhovsky et al. |
| 2011/0295083 A1 | 12/2011 | Doelling et al. |
| 2011/0301670 A1 | 12/2011 | Gross et al. |
| 2012/0041511 A1 | 2/2012 | Lee |
| 2012/0065701 A1 | 3/2012 | Cauller |
| 2012/0083857 A1 | 4/2012 | Bradley et al. |
| 2012/0123498 A1 | 5/2012 | Gross |
| 2012/0130448 A1 | 5/2012 | Woods et al. |
| 2012/0130463 A1 | 5/2012 | Ben-David et al. |
| 2013/0066393 A1 | 3/2013 | Gross et al. |
| 2015/0039046 A1 | 2/2015 | Gross |

FOREIGN PATENT DOCUMENTS

| | | |
|---|---|---|
| WO | 01/10432 | 2/2001 |
| WO | WO200110375 | 2/2001 |
| WO | 01/26729 | 4/2001 |
| WO | 02/09808 | 2/2002 |
| WO | WO2004064729 | 8/2004 |
| WO | WO2009043080 | 4/2009 |
| WO | 2009110935 | 9/2009 |
| WO | WO2011154937 | 12/2011 |
| WO | 2012066532 | 5/2012 |
| WO | 2013111137 | 8/2013 |

OTHER PUBLICATIONS

Eisele D.W., A.R. Schwartz, and P.L. Smith, "Tongue neuromuscular and direct hypoglossal nerve stimulation for obstructive sleep apnea.," Otolaryngologic clinics of North America, vol. 36, 2003, p. 501.

Reid R. Harrison, et al., "Wireless Neural Recording with Single Low-Power Integrated Circuit", IEEE Trans Neural Syst Rehabil Eng. Aug. 2009; 17(4): 322-329.

Hu et al., Percutaneous Biphasic Electrical Stimulation for Treatment of Obstructive Sleep Apnea Syndrome, IEEE Transactions on Biomedical Engineering, Jan. 2008 vol. 55 Issue:1 p. 181-187—an abstract.

Loeb, F.J. Richmond, and L.L. Baker, "The BION devices: injectable interfaces with peripheral nerves and muscles," Neurosurgical focus, vol. 20, 2006, pp. 1-9.

E.A. Mann, T. Burnett, S. Cornell, and C.L. Ludlow, "The effect of neuromuscular stimulation of the genioglossus on the hypopharyngeal airway," The Laryngoscope, vol. 112, 2002, pp. 351-356.

A. Oliven, M. Odeh, L. Geitini, R. Oliven, U. Steinfeld, A.R. Schwartz, and N. Tov, "Effect of coactivation of tongue protrusor and retractor muscles on pharyngeal lumen and airflow in sleep apnea patients," Journal of Applied Physiology, vol. 103, 2007, p. 1662.

A. Oliven, Electrical stimulation of the genioglossus to improve pharyngeal patency in obstructive sleep apnea: comparison of resultsobtained during sleep and anesthesia, U.S. National Library of Medicine, National Institutes of Health May 2009;148(5):315-9, 350, 349—an abstract.

A. Oliven, R.P. Schnall, G. Pillar, N. Gavriely, and M. Odeh, "Sublingual electrical stimulation of the tongue during wakefulness and sleep," Respiration physiology, vol. 127, 2001, pp. 217-226.

A. Oliven, D.J. O'Hearn, A. Boudewyns, M. Odeh, W. De Backer, P. van de Heyning, P.L. Smith, D.W. Eisele, L. Allan, H. Schneider, and others, "Upper airway response to electrical stimulation of the genioglossus in obstructive sleep apnea," Journal of Applied Physiology, vol. 95, 2003, p. 2023.

Patents Galore: Implantable Neurostimulators Fight Snoring and Corpse Eye-Proof Scanners. Printout from httplimedgaclget.com12006/03/patents zalore.html (Downloaded Jan. 2012).

Schwartz A.R., D.W. Eisele, A. Hari, R. Testerman, D. Erickson, and P.L. Smith, "Electrical stimulation of the lingual musculature in obstructive sleep apnea," Journal of Applied Physiology, vol. 81, 1996, p. 643.

A. Oliven, M. Odeh, L. Geitini, R. Oliven, U. Steinfeld, A.R. Schwartz, and N. Toy, "Effect of coactivation of tongue protrusor and retractor muscles on pharyngeal lumen and airflow in sleep apnea patients," Journal of Applied Physiology, vol. 103, 2007, p. 1662.

Tran W.H., G.E. Loeb, F.J.R. Richmond, A.C. Dupont, K.C. Mahutte, C.S.H. Sassoon, and M.J. Dickel, "Development of asynchronous, intralingual electrical stimulation to treat obstructive sleep apnea," Engineering in Medicine and Biology Society, 2003. Proceedings of the 25th Annual International Conference of the IEEE, 2004, pp. 375-378.

Tran W.H., G.E. Loeb, F.J.R. Richmond, R. Ahmed, G.T. Clark, and P.B. Haberman, "First subject evaluated with simulated BIONTM treatment in genioglossus to prevent obstructive sleep apnea," Engineering in Medicine and Biology Society, 2004. IEMBS'04. 26th Annual International Conference of the IEEE, 2005, pp. 4287-4289.

D.J. Young, "Wireless powering and data telemetry for biomedical implants," Engineering in Medicine and Biology Society, 2009. EMBC 2009. Annual International Conference of the IEEE, 2009, pp. 3221-3224.

G.E. Loeb, '•' F J R Richmond, J. Singh, R.A. Peck, W. Tan, Q. Zou, and N. Sachs, "RF-powered BIONsTM for stimulation and sensing," Engineering in Medicine and Biology Society, 2004. IEMBS'04. 26th Annual International Conference of the IEEE, 2005, pp. 4182-4185.

P.R. Troyk, "Injectable electronic identification, monitoring, and stimulation systems," Biomedical Engineering, vol. 1, 1999, p. 177.

T.K. Whitehurst, J.H. Schulman, K.N. Jaax, and R. Carbunaru, "The Bion® Microstimulator and its Clinical Applications," Implantable Neural Prostheses 1, 2009, pp. 253-273.

Chris Seper, "Neuros Medical Launches to Develop New Device to Block Amputee, Chronic Pain", Mar. 16, 2009.

Urgent® PC, Simple Safe. Effective. Neuromodulation System, Uroplasty, Mar. 2009.

"JumpStart and Case Technology Ventures Invest in Neuros Medical", CTV Case Technology Ventures, Mar. 17, 2009.

Theuvenet "Responses to median and tibial nerve stimulation in patients with chronic neuropathic pain", , Brain Topography, vol. 11, No. 4, 1999, pp. 305-313(9)—an abstract.

Armstrong, J, "Is electrical stimulation effective in reducing neuropathic pain in patients with diabetes?", by Foot Ankle Surg. Jul.-Aug. 1997; 36(4): 260-3—an abstract.

Ross Davis, Cerebellar Stimulation for Cerebral Palsy Spasticity, Function and Seizures. Clinical Neuroscience Center, 1999. pp. 290-299.

Dean and Cruse, Motor Pattern Generation, Handbook of Brain Theory and Neural Networks, 1995, pp. 696-701.

Jobges et al., Vibratory proprioceptive stimulation affects Parkinsonian tremor. Parkinsonism & Related Disorders, 8(3), 171-176, Jan. 2002.

(56) References Cited

OTHER PUBLICATIONS

Mones and Weiss, The response of the tremor of patients with Parkinsonism to peripheral nerve stimulation. J. Neurol. Neurosurg. Psychiat. 1969, 32. 512-519.
Y. Zhang, et al. "Optimal Ventricular Rate Slowing During Atrial Fibrillation by Feedback AV Nodal-Selective Vagal Stimulation", Am J Physiol Heart Circ Physiol 282:H1102-H1110, 2002.
Evetovich T.K. et al., Gender comparisons of the mechanomyographic responses to minimal concentric and eccentric isokinetic muscle actions, Medicine & Science in Sports & Exercise, 1998 pp. 1697-1702. Absract.
M. Manfredi, "Differential Block of conduction of larger fibers in peripheral nerve by direct current", Arch. Ital. Biol. 108:52-71, 1970.
Barry S. Russman MD, Cerebral Palsy, CCuiTent Science Inc. 2000.
Sweeney JD et al., "An asymmetric two electrode cuff for generation of unidirectionally propagated action potentials," IEEE Transactions on Biomedical Engineering, vol. BME-33(6) (1986).
Sweeney JD et al., "A Nerve cuff technique for selective excitation of nerve trunk regions," IEEE Transactions on Biomedical Engineering, 37(7) (1990).
Ungar IJ et al., "Generation of unidirectionally propagating action potentials using a monopolar electrode cuff," Annals of Biomedical Engineering, 14:437-450 (1986).
Fitzpatrick et al., in "A nerve cuff design for the selective activation and blocking of myelinated nerve fibers," Ann. Conf. of the IEEE Eng. in Medicine and Biology So, 13(2), 906 (1991).
Rijkhoff NJ et al., "Orderly recruitment of motoneurons in an acute rabbit model," Ann. Conf. of the IEEE Eng., Medicine and Biology Soc., 20(5):2564 (1998).
Van den Honert C et al., "A technique for collision block of peripheral nerve: Frequency dependence," MP-12, IEEE Trans. Biomed. Eng. 28:379-382 (1981).
Baratta R et al., "Orderly stimulation of skeletan muscle motor units with tripolar nerve cuff electrode," IEEE Transactions on Biomedical Engineering, 36(8):836¬43 (1989).
Van den Honert C et al., "Generation of unidirectionally propagated action potentials in a peripheral nerve by brief stimuli," Science, 206:1311-1312 (1979).
M. Devor, "Pain Networks", Handbook of Brand Theory and Neural Networks, ED M.A. Arbib MIT Press pp. 698-702, 1998.
Epilepsy center. http://www.bcm.tmc.edu/neural/struct/epilep/epilsy vagus.html. May 31, 2011 (2 Versions).
J.F. Cortese, "Vagus Nerve Stimulation for Control of Intractable Epileptic Seizures", May 31, 2001.
An International Search Report which issued during the prosecution and a Written Opinion both dated Jul. 11, 2013 of Applicant's PCT/IL2013/005069.
An Office Action dated Dec. 5, 2013, which issued during the prosecution of U.S. Appl. No. 13/528,433.
An International Search Report and a Written Opinion both dated Apr. 17, 2012 which issued during the prosecution of Applicant's PCT/I LI 1/00870.
Office Action issued in U.S. Appl. No. 13/249,062, dated Dec. 13, 2013.
An Office Action dated Feb. 13, 2004, which issued during the prosecution of U.S. Appl. No. 10/254,024.
A Restriction Requirement prosecution of US Patent dated May 11, 2012, which issued during the U.S. Appl. No. 12/946,246.
A Notice of Allowance dated prosecution of US Patent Aug. 26, 2004, which issued during the U.S. Appl. No. 10/254,024.
An Office Action dated Jun. 24, 2011, which issued during the prosecution of U.S. Appl. No. 12/796,102.
An International Search Report 2011, which issued during and a Written Opinion both dated Nov. 14, the prosecution of Applicant's PCT/IL2011/000440.
An International Preliminary Search Repport which issued during the prosecution Report on Patentability dated Dec. 10, 2012, of Applicant's PCT/IL2011/000440.
U.S. Appl. No. 60/263,834, filed Jan. 2, 2001.
An Office Action dated Apr. 9, 2012, which issued during the prosecution of U.S. Appl. No. 12/796,102.
Invitation to pay Additional prosecution of Applicant's Fees dated May 10, 2013 which issued during the PCT/IL2013/005069.
An Office Action dated Sep. 30, 2013, which issued during the prosecution of U.S. Appl. No. 12/796,102.
An International Preliminary Report issued during the prosecution on Patentability dated May 21, 2013 which of Applicant's PCT/IL11/00870.
An Office Action dated Sep. 3, 2014 which issued during the prosecution of U.S. Appl. No. 13/885,360.
U.S. Appl. No. 61/591,024, filed Jan. 26, 2012.
U.S. Appl. No. 61/662,073, filed Jun. 20, 2012.

\* cited by examiner

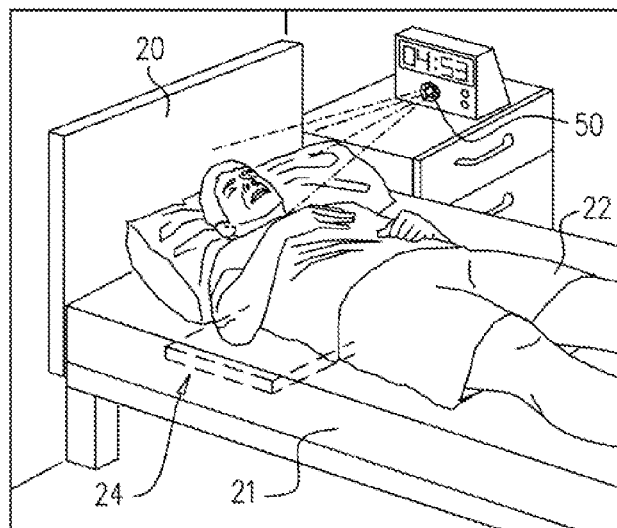
FIG. 1
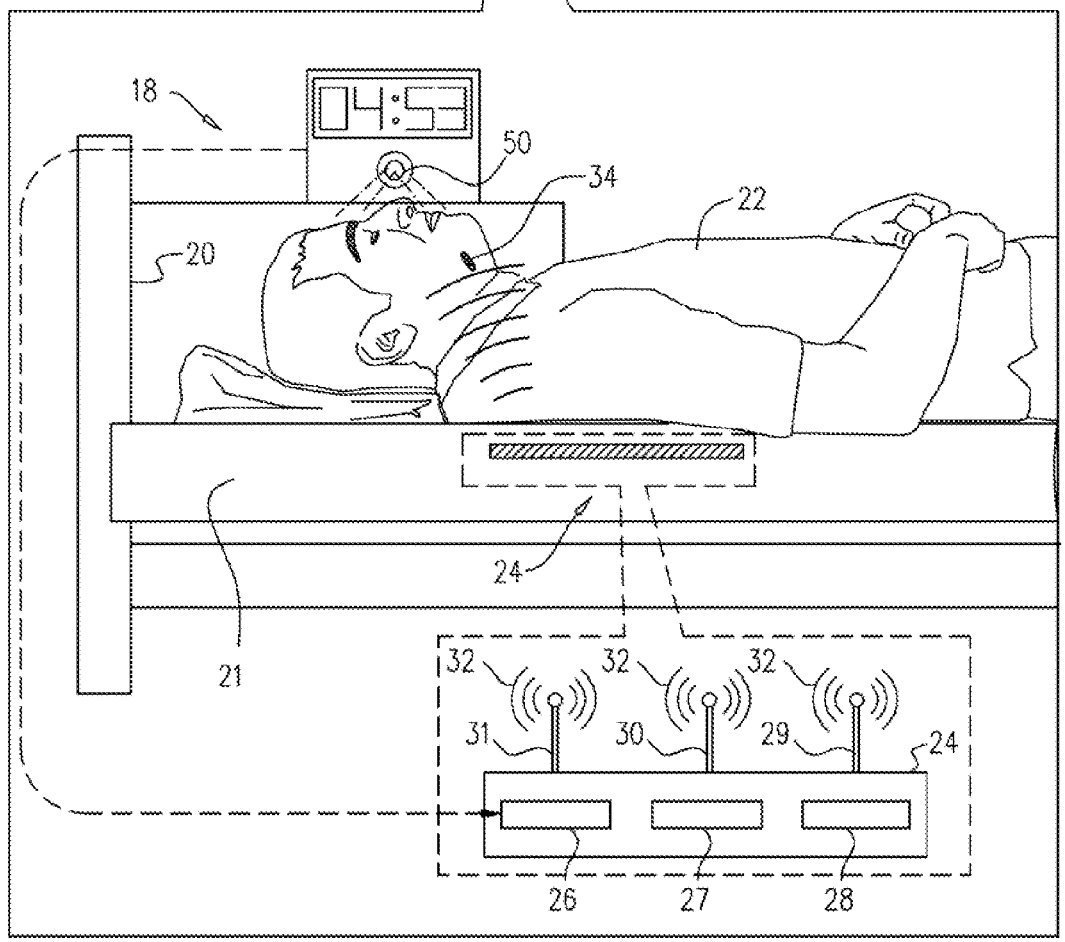

SLEEP APNEA TREATMENT

CROSS-REFERENCE TO RELATED APPLICATIONS

The present application is a continuation-in-part of U.S. patent application 13/885,360 to Gross (published as US 2013/0261693), entitled "Sleep apnea treatment system," which is the US national phase of PCT/IL2011/000870 (published as WO 2012/066532), filed Nov. 10, 2011, which is a continuation-in-part of U.S. patent application Ser. No. 12/946,246 to Gross (published as US 2012/0123498) entitled "Sleep apnea treatment system," filed Nov. 15, 2010, now abandoned. The above-mentioned applications are incorporated herein by reference.

FIELD OF THE INVENTION

Some applications of the present invention generally relate to implanted medical apparatus with an external power and control source. Specifically, some applications of the present invention relate to apparatus and methods for treating sleep apnea, particularly, obstructive sleep apnea (OSA).

BACKGROUND

Sleep apnea is a chronic sleep breathing disorder typically characterized by abnormal pauses (apneas) in an individual's breathing, or alternatively, by instances of abnormally low breathing. Each apnea event can range in duration from seconds to minutes. Sleep apnea, although often unrecognized for years by the subject herself, can have long term health effects: Sleep apnea and other sleep breathing disorders are associated with cardiovascular disease, myocardial infarction, high blood pressure, stroke, arrhythmias, diabetes, sleep-deprived driving accidents, and cerebrovascular disease.

In general, there are three forms of sleep apnea: central sleep apnea (CSA), obstructive sleep apnea (OSA), and complex sleep apnea—a heterogeneous group of sleep-related breathing disturbances, with characteristics partially related to both CSA and OSA.

With CSA, cessations in air flow occur without respiratory effort. With OSA (alternatively, obstructive sleep apnea/hypopnea syndrome (OSAHS)), which has overlapping pathogenesis and clinical presentation with CSA, in subject's breathing is interrupted by a physical blockage in the airflow, often characterized, but not limited to snoring and restless sleep. Cardiac output also tends to decrease during apnea events. Snoring, along with other risk factors such as obesity, diabetes or smoking, is often indicative of OSA, particularly when snoring is punctuated by deep gasps.

OSA, the most common form of sleep apnea, is characterized by repetitive collapse and reopening of the upper airway during sleep, resulting in complete or partial blockage of the upper airway during sleep and leading to hypoxemia and hypercapnia. Typically, dilator muscles in the subject's airway stiffen and dilate various regions of the upper airway while the subject is awake. This activity, however, is reduced during sleep, effectively narrowing the upper airway. Of the dilator muscles, the largest is the genioglossus, (the muscle that forms the majority of the tongue).

Current treatments includes positive airway pressure (PAP) therapy, particularly, continuous positive expiratory pressure (CPAP), oral appliances, surgery, including genioglossus advancement, tongue radiofrequency treatment, midline glossectomy, hyoid suspension, maxillomandibular advancement, and lifestyle changes such as positional therapy and weight loss.

SUMMARY OF THE INVENTION

For some applications of the invention, apparatus for treating obstructive sleep apnea comprises a breathing sensor for sensing breathing activity, configured for placement outside of a body of a subject, e.g., in a mattress or an article of clothing. Breathing can be sensed by, for example, sensing electrical activity, breathing-related motions, or via video imaging of the subject's respiration. The apparatus typically also has a control unit, coupled to the breathing sensor, configured to generate signals in response to the sensed activity associated with breathing. The apparatus further typically has a power unit that powers the breathing sensor, the control unit and an implant, e.g., a sublingual implant. The implant typically comprises a wireless receiver for receiving signals, two or more electrodes, circuitry coupled to the electrodes, and one or more coils coupled to the circuitry to wirelessly receive power from the external device. Typically, the circuitry drives the electrodes to apply current to a sublingual muscle site, or in some applications, to a sublingual nerve site, or in further applications, at a phrenic nerve site, of the subject in response to the signal.

In some applications, an imaging device is used to generate images of the subject while the subject sleeps. Based on a set of training images received from the imaging device, the control unit learns an association between a position of the subject's head and OSA of the subject, i.e., the control unit learns which head positions are associated with a higher frequency and/or severity of OSA, relative to other head positions. In response to the learned association, the control unit establishes thresholds for an OSA-related parameter, such as snoring intensity or breathing volume, that are different for different head positions. Then, at a given time subsequent to the learning, the control unit treats the subject for OSA only if the value of the OSA-related parameter passes the threshold that corresponds to the head position of the subject at the given time. For example, if the subject's head is in the supine position, the control unit may decide to treat the subject if the snore decibel level reaches 50 dB; for a different head position, however, the control unit might not treat the subject unless the snore decibel level reaches 70 dB.

There is therefore provided, in accordance with an application of the present invention, apparatus for treating obstructive sleep apnea, comprising:
an external device, comprising:
  a breathing sensor configured for placement outside of a body of a subject, and to sense activity associated breathing of the subject; and
  a control unit, coupled to the breathing sensor, configured to generate a signal in response to the sensed activity; and
an implant, comprising:
  a wireless receiver for receiving the signal;
  two or more electrodes; and
  circuitry coupled to the electrodes, the circuitry configured to drive the electrodes to apply current to an anatomical site of the subject in response to the signal, in a plurality of successive periods of inspiration of the subject, even in the absence of a detection of apnea by the control unit.

In an application, the implant is configured to be implanted sublingually.

In an application, the implant configured to stimulate a phrenic nerve of the subject.

In an application, the implant is configured to stimulate breathing muscles associated with a phrenic nerve of the subject.

In an application, the external device is configured to be coupled to a mattress.

In an application, the external device in configured to be coupled to an article of clothing.

In an application, the two or more electrodes are configured to be coupled to a sublingual muscle of the subject.

In an application, the implant comprises at least two antennas that are not aligned in a same direction, and wherein the implant is configured to receive the signal via the at least two antennas.

In an application, the breathing sensor is configured to sense a parameter selected from the group consisting of: airway pressure, snoring sounds, snoring motions, mechanical motion, and electrical activity associated with respiration.

In an application, the implant is operative to vary at least one parameter of the applied current, the parameter selected from the group consisting of: a frequency of pulses of the current, an amplitude of pulses of the current, and duration of pulses of the current.

In an application, the implant comprises an implant sensor configured to provide feedback to the external device.

In an application, the control unit is configured to generate the signal during respective inspiratory phases of at least 30% of respiratory periods of the subject in a ten-minute period.

In an application, the external device comprises a power supply unit, which is configured to supply power wirelessly to the implant.

In an application, the implant comprises at least two antennas that are not all in a same direction, and wherein the implant is configured to receive the power via the at least two antennas.

In an application, the two or more electrodes are configured to be coupled to a sublingual nerve of the subject.

In an application, the implant comprises a nerve cuff to which the electrodes are coupled.

There is further provided, in accordance with an application of the present invention, a method for treating obstructive sleep apnea, comprising:
identifying a subject as suffering from obstructive sleep apnea; and
in response, implanting an implant that is configured to:
stimulate an anatomical site in at plurality of successive periods of inspiration of the subject, even in the absence of a detection of apnea; and
wirelessly receive energy from an external device, to power the implant.

In an application, implanting the implant comprises implanting the implant in a vicinity of a phrenic nerve of the subject.

In an application, implanting the implant comprises implanting the implant, the implant being configured to stimulate the site in response to an identification of an Inspiration period by an external device, and to withhold the stimulation of the site during at least a portion of an expiration period identified by the external device, in response to the identification of the expiration period by the external device.

In an application, the method further includes configuring the external device to sense breathing of the subject and to provide a signal, to the implant to cause the implant to directly stimulate the muscle in response to the sensing of the breathing by the external device, during respective inspiratory phases of at least 30% of respiratory periods in an hour.

In an application, implanting the implant comprises implanting the implant at a sublingual site of the subject.

In an application, implanting the implant comprises implanting the implant, the implant being configured to stimulate the sublingual site in response to an identification of an inspiration period by an external device, and to withhold the stimulation of the sublingual site during at least a portion of an expiration period identified by the external device, in response to the identification of the expiration period by the external device.

In an application, implanting the implant comprises sublingually injecting the implant.

In an application, implanting the implant comprises placing the implant in a position to stimulate a sublingual muscle of the subject.

In an application, implanting the implant comprises placing the implant in a position to stimulate a sublingual nerve of the subject.

There is further provided, in accordance with an application of the present invention, a method for using an implant to treat obstructive sleep apnea, comprising:
configuring an external device to:
sense breathing of the subject;
provide a signal to the implant to cause the implant to directly stimulate an anatomical site in response to the sensing of the breathing by the external device, even in the absence of a detection of apnea, during respective inspiratory phases of at least 30% of respiratory periods in a ten-minute period; and
wirelessly transmit energy from the external device to the implant to power the implant.

In an application, providing the signal comprises providing the signal, the external device being configured to provide a signal to the implant to cause the implant to directly stimulate the anatomical site in response to the sensing of the breathing by the external device, even in the absence of a detection of apnea, during respective inspiratory phases of at least 50% of respiratory periods in a ten-minute period;

In an application, configuring the device to provide the signal comprises configuring the device to provide the signal to a sublingual implant.

In an application, configuring the device to provide the signal comprises configuring the device to provide the signal to a phrenic nerve implant.

There is further provided, in accordance with an application of the present invention, a method for treating obstructive sleep apnea, comprising:
identifying a subject as suffering from obstructive sleep apnea; and
in response to the identifying, sublingually implanting a sublingual implant in the subject, the implant being configured to provide feedback regarding breathing of the subject to an external device and to receive from the external device a signal that (a) is generated by the external device in response to the feedback provided by the sublingual implant, and (b) causes the implant to stimulate a sublingual site of the subject.

In an application, the method further includes coupling the external device to an article of clothing.

In an application, the method further includes configuring the external device to sense breathing and to provide the signal in response to the feedback provided by the sublingual implant and in response to the breathing sensed by the external device.

In an application, implanting the sublingual implant configured to provide feedback regarding breathing, comprises implanting a sublingual implant configured to provide feedback regarding snoring of the subject.

In an application, the method further includes juxtaposing the external device to a household item.

In an application, juxtaposing the external device comprises juxtaposing the external device to a part of a bed.

There is further provided, in accordance with an application of the present invention, a method for treating obstructive sleep apnea, comprising:

identifying a subject as suffering from obstructive sleep apnea; and in response to the identifying, implanting a phrenic nerve implant in the subject the implant being configured to provide feedback regarding breathing of the subject to an external device and to receive from the external device a signal that (a) is generated by the external device in response to the feedback provided by the phrenic nerve implant, and (b) causes the implant to stimulate an anatomical site of the subject in the vicinity of the phrenic nerve.

There is further provided, in accordance with an application of the present invention, a method for treating obstructive sleep apnea of a subject, the method comprising:

extracorporeally detecting breathing of the subject;

automatically extracorporeally generating a signal, at least in part responsively to the detected breathing;

intracorporeally detecting the signal; and automatically stimulating a site of the subject, at least in part responsively to the signal, the site selected from the group consisting of: a sublingual muscle of the subject and a phrenic nerve of the subject.

In an application, the method further includes extracorporeally detecting reclining of the subject, wherein automatically extracorporeally generating the signal comprises automatically extracorporeally generating the signal at least in part responsively to the reclining of the subject.

In an application, the method further includes intracorporeally detecting reclining of the subject, wherein automatically stimulating the sublingual muscle of the subject comprises automatically stimulating the sublingual muscle of the subject at least in part responsively to the reclining of the subject.

In an application, extracorporeally detecting the breathing comprises extracorporeally detecting the breathing while the subject is sleeping.

In an application, intracorporeally detecting the signal comprises wirelessly receiving power via the signal, using an implant, and wherein automatically stimulating the site of the subject comprises powering the implant using the received power.

There is further provided, in accordance with some applications of the present invention, apparatus for treating a subject for obstructive sleep apnea (OSA), the apparatus including:

an implant, including:
a wireless receiver;
two or more electrodes; and
circuitry coupled to the electrodes;
an imaging device configured to generate images of the subject while the subject sleeps;
at least one antenna; and
a control unit configured to:
at a first time, in response to a set of training images received from the imaging device:
learn an association between a position of a head of the subject and OSA of the subject, and
in response to the association, establish, for an OSA-related parameter, at least two distinct thresholds corresponding to respective different head positions, and
at as second time following the first time, in response to a second-time position of the subject's head exhibited in a second-time image received from the imaging device:
select, from the established thresholds, a threshold that corresponds to the second-time position of the subject's head, and
if a second-time value of the OSA-related parameter passes the selected threshold, treat the subject for OSA by driving the antenna to transmit a signal to the wireless receiver, the wireless receiver being configured to receive the signal, and the circuitry being configured to drive the electrodes to apply current to an anatomical site of the subject in response to the received signal.

In some applications, the implant is configured to be implanted sublingually.

In some applications, the two or more electrodes are configured to be coupled to a sublingual muscle of the subject.

In some applications, the apparatus further includes a breathing sensor configured to sense the second-time value of the OSA-related parameter by sensing activity associated with breathing of the subject.

In some applications, the breathing sensor is configured to sense activity associated with breathing of the subject by sensing a phenomenon selected from the group consisting of: airway pressure, snoring sounds, snoring motions, mechanical motion, and electrical activity.

There is further provided, in accordance with some applications of the present invention, a method for treating a subject for obstructive sleep apnea (OSA), the method including:

using an imaging device, generating a set of training images of the subject while the subject sleeps;
using a control unit:
in response to the set of training images, learning an association between a position of a head of the subject and OSA of the subject; and
in response to the association, establishing, for an OSA-related parameter, at least two distinct thresholds corresponding to respective different head positions;
using the imaging device, generating a second-time image of the subject while the subject sleeps; and
using the control unit, in response to a second-time position of the subject's head exhibited in the second-time image:
selecting, from the established thresholds, a threshold that corresponds to the second-time position of the subject's head, and
if a second-time value of the OSA-related parameter passes the selected threshold, treating the subject for OSA by driving an implant to apply current to an anatomical site of the subject.

In some applications,
the method is for use with at least one antenna,
the implant includes a wireless receiver, two or more electrodes, and circuitry coupled to the electrodes, and
treating the subject includes:
using the control unit to drive the antenna to transmit a signal to the wireless receiver; and
using the circuitry, driving the electrodes to apply current to the anatomical site of the subject, in response to the signal.

In some applications, the method further includes implanting the implant in the subject.

In some applications, implanting the implant in the subject includes sublingually implanting the implant.

In some applications, the method further includes using a breathing sensor to sense the second-time value of the OSA-related parameter by sensing activity associated with breathing of the subject.

In some applications, sensing activity associated with breathing of the subject includes sensing activity associated with breathing of the subject by sensing a phenomenon selected from the group consisting of: airway pressure, snoring sounds, snoring motions, mechanical motion, and electrical activity.

There is further provided in accordance with some applications of the present invention, apparatus for treating a subject for obstructive sleep apnea (OSA), the apparatus including:

an implant, including:
a wireless receiver;
two or more electrodes; and
circuitry coupled to the electrodes;
an imaging device configured to generate images of the subject while the subject sleeps;
at least one antenna; and
a control unit configured to:
at a first time, in response to a set of training images received from the imaging device, learn an association between a position of a head of the subject and OSA of the subject, and
at a second time following the first time, in response to (a) a second-time position of the subject's head exhibited in a second-time image received from the imaging device, and (b) the learned association, treat the subject for OSA by driving the antenna to transmit a signal to the wireless receiver, the wireless receiver being configured to receive the signal, and the circuitry being configured to drive the electrodes to apply current to an anatomical site of the subject in response to the received signal.

There is further provided, in accordance with some applications of the present invention, a method for treating a subject for obstructive sleep apnea (OSA), the method including:

using an imaging device, generating a set of training images of the subject while the subject sleeps;
using a control unit, in response to the set of training images, learning an association between a position of a head of the subject and OSA of the subject;
using the imaging device, generating a second-time image of the subject while the subject sleeps; and
using the control unit, in response to (a) a second-time position of the subject's head exhibited in the second-time image, and (b) the learned association, treating the subject for OSA by driving an implant to apply current to an anatomical site of the subject.

The present invention will be more fully understood from the following detailed description of applications thereof, taken together with the drawings, in which:

BRIEF DESCRIPTION OF THE DRAWINGS

FIG. 1 is a schematic illustration of a system including an external device and a sublingual implant, in accordance with some applications of the present invention;

DETAILED DESCRIPTION OF APPLICATIONS

Figure 2:
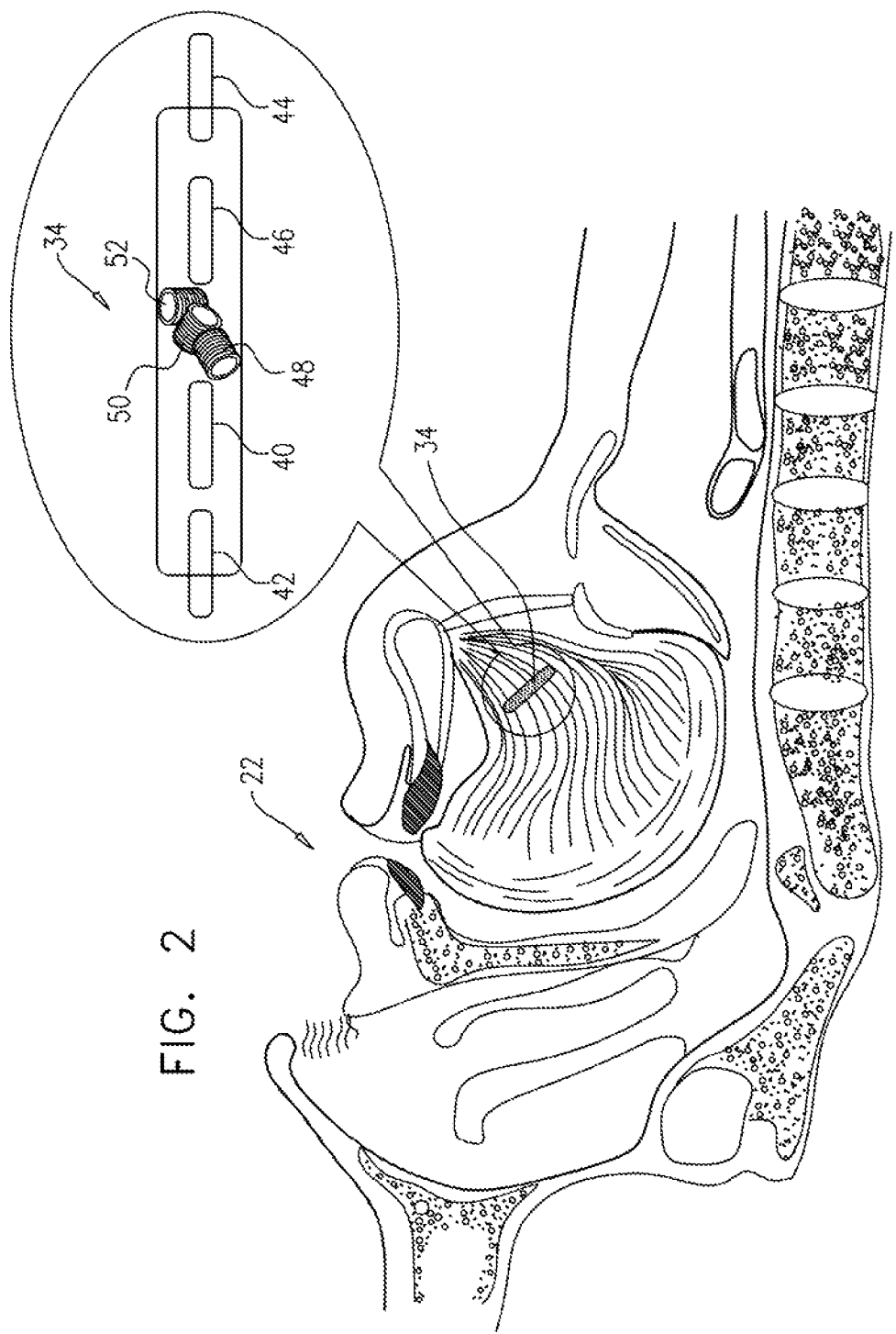
FIG. 2 is a schematic illustration of the sublingual implant of FIG. 1, in accordance with some applications of the present invention.

Reference is now made to FIG. 1, which is a schematic illustration of a bed 20 and a subject 22 lying supine on a mattress 21 of bed 20. Typically, the subject is sleeping. A system 18 is provided, which comprises an external device 24 and a sublingual implant 34, typically implanted at an anatomical site in the vicinity of sublingual muscles. Except for differences as noted, sublingual implant 34 is generally as described in U.S. patent application Ser. No. 12/946,246 to Gross, filed Nov. 15, 2010, now abandoned, which is incorporated herein by reference, in accordance with some applications of the present invention.

In further applications, system 18 comprises an external device 24 and a phrenic nerve implant (not shown), typically implanted at an anatomical site in the vicinity of the phrenic nerve.

External device 24 comprises a control unit 26, a breathing sensor 28 and at least one power supply unit 27. Control unit 26 typically comprises a computer processor, input/output ports, and/or other computer components and/or other electronic circuitry. External device 24, in accordance with some applications of the present invention, is placed in proximity to the subject, typically by being incorporated into the subject's mattress 21. Alternatively, the external device can be placed anywhere near the subject, such that sublingual implant 34 receives signals from the external device. In some applications, external device 24 is placed in a chest band, in another article of clothing of the subject (e.g., a cap), or at another site near the subject. One or more antennas 29, 30, and 31 of external device 24 are typically configured to send signals to the implant, as described hereinbelow. The configuration of antennas 29, 30, and 31 as shown it FIG. 1 are for illustrative purposes only. Typically, the antennas are not configured to be positioned in a straight line. In a further application, the antennas are not aligned in a same direction, e.g., the antennas are mutually perpendicular.

External device 24 is typically always powered on and, in some applications, does not have an on/off switch. In other applications, external device 24 is in standby mode, powering on to its active mode when the breathing of subject 22 is detected. In some applications, external device 24 is coupled to sensors, e.g., pressure sensors (not shown), to detect when subject 22 is lying down on mattress 21. The sensors are configured to communicate with external device 24, resulting in the powering on of external device 24 to its active mode in response to the lying down of subject 22.

In some applications, in which external device 24 is not continuously in powered on and active mode, e.g., when external device 24 is either completely powered off or in a stand-by mode, the device, when turned on, remains in the powered-on mode for a set duration, such as 5-120 minutes (e.g., 30 minutes). In other applications, the duration for which the external device remains powered-on can be configured to be a desired length of time.

In some applications, in which external device 24 is not continuously in powered on and active mode, e.g., when external device 24 is either completely powered-off or in a stand-by mode, the device powers on in response to the detection of a sleep-related breathing rate by breathing sensor 28. In further applications, external device 24 is configured to power-down in the morning, when breathing sensor 28 detects waking levels of breathing, or other indications of subject 22 being awake.

In some applications, breathing sensor 28 has a separate powered cycle than the other components of external device 24. For example, breathing sensor 28 may be powered separately from the other components in the external device.

Power supply unit 27 is configured to wirelessly charge sublingual implant 34, typically via induction, but other methods known in the art may also be used. Power supply unit 27 allows sublingual implant 34 to be constantly in a powered-on mode, typically without concern for draining batteries of the sublingual implant. In further applications, power supply unit 27 is configured to wirelessly charge the phrenic nerve implant, allowing the phrenic nerve implant to be constantly in a powered-on mode, typically without concern for draining batteries of the implant.

When powered-on constantly in its active mode, or in other applications, when the external device is triggered by an event to power-on, external device 24 sends signals to sublingual implant 34 during or shortly after the event (for example, an abnormal breathing episode). In further applications, external device 24 sends signals to the phrenic nerve implant during or shortly after the event (for example, an abnormal breathing episode).

Typically one or more antennas 29, 30, 31 are configured to be in communication with power supply unit 27 to wirelessly power either sublingual implant 34 or the phrenic nerve implant. In some applications, at least two antennas 29 and 31 are configured to send signals such that regardless of the position of subject 22, a sufficient amount of power will be typically received by sublingual implant 34. In other applications, at least two antennas 29 and 31 are configured to send signals such that regardless the position of subject 22, a sufficient amount of power will be received by the phrenic nerve implant. In some applications, the antennas are placed in a triangular formation. In some applications, the antennas are mutually-perpendicular antennas.

In some applications, antenna 30 is also configured to send power to sublingual implant 34 and/or the phrenic nerve implant, either in lieu of, or in addition to, antennas 29 and 31.

Typically, the breathing sensor senses respiration, and control unit 26 sends signals 32 responsive thereto to sublingual implant 34, typically implanted in at muscle (e.g., the genioglossus muscle). In other applications, sublingual implant 34 is implanted on, at, or near a nerve that innervates at sublingual muscle of the subject. In some applications, sublingual implant 34 is implanted at or near the glossopharyngeal nerve. In further applications, sublingual implant 34 is implanted at or near the hypoglossal nerve. In some applications, a nerve cuff is used to stimulate a nerve in the vicinity of a sublingual muscle of the subject.

In some applications, external device 24 sends signals 32 to the phrenic nerve implant to stimulate the phrenic nerve or surrounding muscle for a pre-determined length of time, or in a particular pattern, or both, over the course of the sleep cycle of subject 22. Typically, the phrenic nerve stimulator is coupled directly to the phrenic nerve (not shown). In further applications, the phrenic nerve implant is implanted an a vein, and provides transvenous phrenic nerve stimulation.

External device 24 typically sends signals 32 to sublingual implant 34, which drive the sublingual implant to stimulate a sublingual muscle or nerve, as described hereinabove. The signals are typically sent to the implant at a particular temporal point in the subject's breathing pattern. In some applications, the temporal point is determined by breathing sensor 28. In some applications, the sublingual implant directly or indirectly stimulates a nerve that innervates a sublingual muscle, the stimulation being configured to cause the nerve, in response, to stimulate the sublingual muscle. In further applications, the signals are sent to the implant at a particular point in time, such that stimulation of the anatomical site during at least a portion of an expiration period identified by the external device is withheld, e.g., there is no stimulatory signal provided by external device 24 during expiration.

In further applications, external device 24 typically sends signals 32 to the phrenic nerve implant, which drive the phrenic nerve implant to stimulate breathing muscles. The signals are typically sent to the implant during a particular, predesignated portion of the subject's breathing pattern. In some applications, the phases of the breathing pattern are determined in real-time by breathing sensor 28. In some applications, the phrenic nerve implant directly or indirectly stimulates a nerve that innervates a breathing muscle, the stimulation being configured to cause the nerve, in response, to stimulate the muscle.

The stimulation of muscle is typically in a plurality of successive periods of respiratory inspiration of subject 22, and, in some applications, even in the absence of a detection of apnea by external device 24.

For some applications, signals 32 are sent to the implant to cause the implant to stimulate the muscle and/or nerve at a non-inspiration point, or at multiple points during a respiratory cycle.

In some applications, external device 24 sends signals 32 to sublingual implant 34, or in some applications, to the phrenic nerve implant, to stimulate the muscle and/or nerve for a pre-determined length of time, or in a particular pattern, or both, over the course of the sleep cycle of subject 22. In some applications, periods of no stimulation by sublingual implant 34, and in some applications, the phrenic nerve implant, are provided, during the course of the sleep cycle, to prevent over-stimulating a muscle and/or nerve (e.g., the genioglossus muscle).

Typically, signals 32 are provided to sublingual implant 34, and in some applications, the phrenic nerve implant, during at least 30% or at least 50% of the respiratory periods over the course of a ten-minute period, even in the absence of detection of apnea by external device 24.

Typically, external device 24 is typically configured to only provide signals 32 to the sublingual implant 34, or in some applications, the phrenic nerve implant, to stimulate a muscle and/or nerve when the subject 22 is sleeping and in the vicinity of external device 24 (e.g., in mattress 21 of bed 20, or in another item near bed 20).

In some applications, breathing sensor 28 is coupled to mattress 21. In further applications, breathing sensor 28 is housed within mattress 21. Breathing sensor 28 typically comprises a piezoelectric crystal, a strain gauge a pressure sensor, an accelerometer, an optical sensor, an audio sensor, a video imager, and/or a cardiac sensor, or combinations thereof, to detect, for example, breathing-related motions, snoring, electrical activity, and/or other indications of the subject's breathing. The one or plurality of sensors provide information regarding, but not limited to, the subject's airway pressure, snoring sounds and motions, mechanical motion associated with respiration, and/or electrical activity associated with respiration. In addition, other sensors known in the art (e.g., a blood oxygen saturation sensor) may assess the operation of external device 24 and implant 34, and support closed-loop control of external device 24 and implant 34, and/or the phrenic nerve implant.

Reference is now made to FIG. 2, which is a schematic illustration of sublingual implant 34 in subject 22, in accordance with some applications of the present invention. Sublingual implant 34 shown in FIG. 2 is typically the sublingual implant described hereinabove with reference to FIG. 1. Sublingual implant 34, shown enlarged, contains a wireless receiver 40, two or more electrodes 42 and 44, and circuitry coupled to the electrodes. In some applications, sublingual implant 34 has one or more power receiving antennas 48, 50 and 52. In further applications, sublingual implant 34 has one or more power receiving antennas oriented in x, y and z directions, configured such that regardless of the position of subject 22, a sufficient amount of power will be received by the antenna. In some applications, the antennas are mutually-perpendicular antennas. In some applications the mutually-perpendicular antennas comprise three coils, each oriented in one of the x, y and z directions.

The implant and its components are encapsulated using techniques known in the art. Material for the electrodes may be chosen based on numerous criteria, as are known in the art, including tissue response, allergic response, electrode-tissue impedance, and radiographic visibility.

Circuitry 46 is typically configured to drive electrodes 42 and 44 to apply current, typically as a train of pulses, to a sublingual site of subject 22 (as described hereinabove), in response to signals 32 from external device 24, in a plurality of successive periods of inspiration of the subject. Typically, signals 32 are generated substantially for the duration of any given sleep cycle, even in the absence of a detection of apnea by the external device. Alternatively, signals 32 are generated for only a portion of the sleep cycle, e.g., for at least 30% or at least 50% of the cycle.

It is to be noted that the sublingual implant's particular location in the muscle is shown by way of illustration and not limitation.

In some applications, sublingual implant 34 includes an implant sensor (not shown), such as a vibration sensor sensitive to snoring vibrations, or a motion sensor. The implant sensor allows the implant to operate independently of, or in conjunction with, external device 24, optionally providing feedback to the external device. In other applications, one or more other implant sensors are included in the implant to be used independently by the implant, or in conjunction with external device 24.

In some applications, the operation parameters of sublingual implant 34 —e.g., duty cycle, frequency, pulse duration or amplitude, of the sublingual implant's current, can be altered in response to how effective or painless the current generated by the implant is, and/or whether the implant disrupts the subject's sleep. This may be done with a wand (not shown), or with an input unit such as a keypad (not shown) on external device 24.

Feedback parameters for determining the efficacy and/or efficiency of the implant are obtained via receiving information from subject 22 himself, by way of sensors in external device 24, or in some applications, by feedback sensors (such as vibration or acceleration sensors, not shown) in sublingual implant 34.

It is noted that the number of sublingual implants shown in the figures is by way of illustration and not limitation. One or more of the implants are typically injected into the subject in a minimally-invasive manner, in an outpatient procedure. Typically, this is done through the lumen of a needle (not shown) using aseptic technique and with local anesthesia, as is known in the art. Other surgical procedures known in the art may also be used to place the implant in a muscle.

For some applications, one or more implants 34 are configured to work in conjunction with other implants or independent of each other and/or external device 24.

Typically, sublingual implant 34 is also configured to wirelessly receive power from external device 24, e.g., via a coil, e.g., coil 48, coupled to circuitry 46. Other applications may use any one of, or a combination of, forms of wireless energy transfer, such as inductive coupling, RF, ultrasound, or other forms of wireless energy transfer.

In some applications, sublingual implant 34 is continuously provided with the necessary power to stimulate the muscle or nerve via power supply unit 27, external device 24, or some other external device (not shown), in close enough proximity to wirelessly transfer power to the implant, as described hereinabove with reference to FIG. 1.

In some applications, sublingual implant 34 can temporarily store electrical power, e.g., by use of a battery or high-capacity capacitor (not shown), coupled by a wire (not shown) to the implant, or disposed within the implant.

In some applications, sublingual implant 34 has an internal battery that is periodically charged by power supply unit 27 or some other external device (not shown), in close enough proximity to wirelessly transfer power to the implant from power supply unit 27, or a different power source (not shown), For some applications, external device 24 operates substantially throughout the night, e.g., causing sublingual implant 34 to drive current into the sublingual muscle and/or sublingual nerve during most respiration cycles. Alternatively, external device 24 determines if the subject is sleeping, and only drives implant 34 during these periods (e.g., only during inspiration during sleep). Further alternatively, external device 24 determines if the subject is snoring, or exhibiting another respiration problem, and only drives the implant during such periods. Other operating parameters have been described hereinabove with reference to FIG. 1. These parameters are described by way of example and illustration but not limitation; other parameters for powering and monitoring sublingual implant 34 and external device 24 are also included within the scope of the present invention.

The aforementioned description of FIG. 2, described hereinabove with relation to sublingual implant 34 is also applicable to the phrenic nerve implant (not shown) with the difference described below: the phrenic nerve implant is typically implanted in the vicinity of the phrenic nerve (e.g., near the phrenic nerve or surrounding or otherwise in contact with the phrenic nerve).

The inventor of the present invention has realized that there may be an important causal relationship between the position of the head during sleep, and the onset and/or severity of OSA. As will now be described, some applications of the present invention make use of this relationship to improve the manner in which OSA treatment is administered.

Figure 3A:
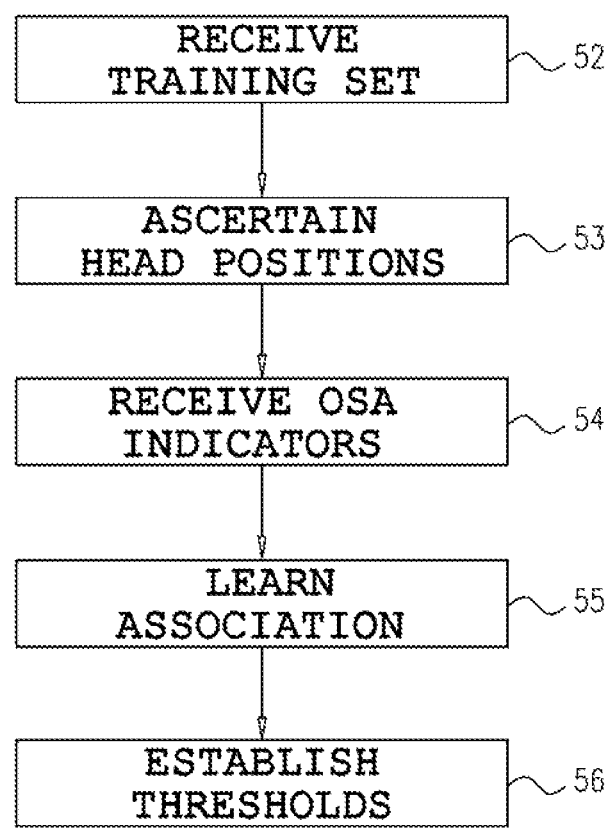
FIG. 3A shows a threshold-establishing flowchart, in accordance with some applications of the present invention.

Reference is again made to FIG. 1, and is also made to FIG. 3A, which shows a threshold-establishing flowchart, in accordance with some applications of the present invention. In some applications, system 18 further comprises an imaging device 50, e.g., a visible-light and/or infrared (IR) camera, which is configured to generate images of the subject while the subject sleeps. At a training-set-receiving step 52, control unit 26 receives a set of training images from imaging device 50. The training set typically includes images of the subject in various sleeping positions; in particular, the training images typically include various head positions of the subject. At a head-position-ascertaining step 53, the control unit uses image-processing and/or computer vision methods known in the art to ascertain the position of the subject's head in each of the training images. At an OSA-indicator-receiving step 54, the control unit receives an OSA indicator for each of the training images, the OSA indicator being indicative of whether an episode of OSA was occurring at the time the image was obtained, and/or a degree of severity of the OSA episode. (Step 54 may occur prior to step 53.)

At a first time, at an association-learning step 55, the control unit learns an association between a position of the subject's head and OSA of the subject. For example, the control unit may learn that images showing the subject's head in a supine position have a greater corresponding frequency and/or severity of OSA, as indicated by the OSA indicators, relative to other images. In other words, the control unit learns that the subject's OSA is more frequent and/or severe when his head is in a supine position, i.e., the supine head position is more associated with OSA than are other head positions.

By way of introduction to the description below, it is noted that in the context of the claims and description of the present application, the term "OSA-related parameter" should be construed to mean any parameter that may reflect an upcoming or presently-occurring episode of OSA. For example, a snore decibel level, a breathing volume (obtained, for example, via image-processing of IR images), and a number of breaths per minute are all OSA-related parameters. While extreme values of OSA-related parameters are typically indicative of an upcoming or presently-occurring OSA episode, moderate values may be difficult to interpret. For example, it is difficult to interpret a snore decibel level of 40 dB, 50 dB, or even 60 dB, since non-OSA-related snoring may occur at any of these decibel levels.

In general, an objective of applications of the present invention is to administer treatment as soon as an OSA episode is anticipated or observed, but not to administer treatment unnecessarily. This objective may be difficult to achieve solely on the basis of the OSA-related parameters, since, as noted above, moderate values of OSA-related parameters may be difficult to interpret. Applications of the present invention address this problem, by providing thresholds for at least one OSA parameter. This occurs at a threshold-establishing step 56, at which, in response to the association, the control unit establishes thresholds for an OSA-related parameter. These thresholds facilitate the decision as to whether to administer treatment to the subject.

The thresholds include at least two distinct thresholds corresponding to respective different head positions. For example, for the snore decibel level parameter, the control unit may establish a threshold of 50 dB for a supine head position, and 70 dB for a non-supine head position, if the supine head position is more associated with OSA than the non-spine head position. This means that, if the subject's head is in the supine position, the control unit may decide to treat the subject if the snore decibel level reaches 50 dB; for other head positions, however, the control unit might not treat the subject unless the snore decibel level reaches 70 dB. This example will be generalized immediately hereinbelow.

Figure 3B:
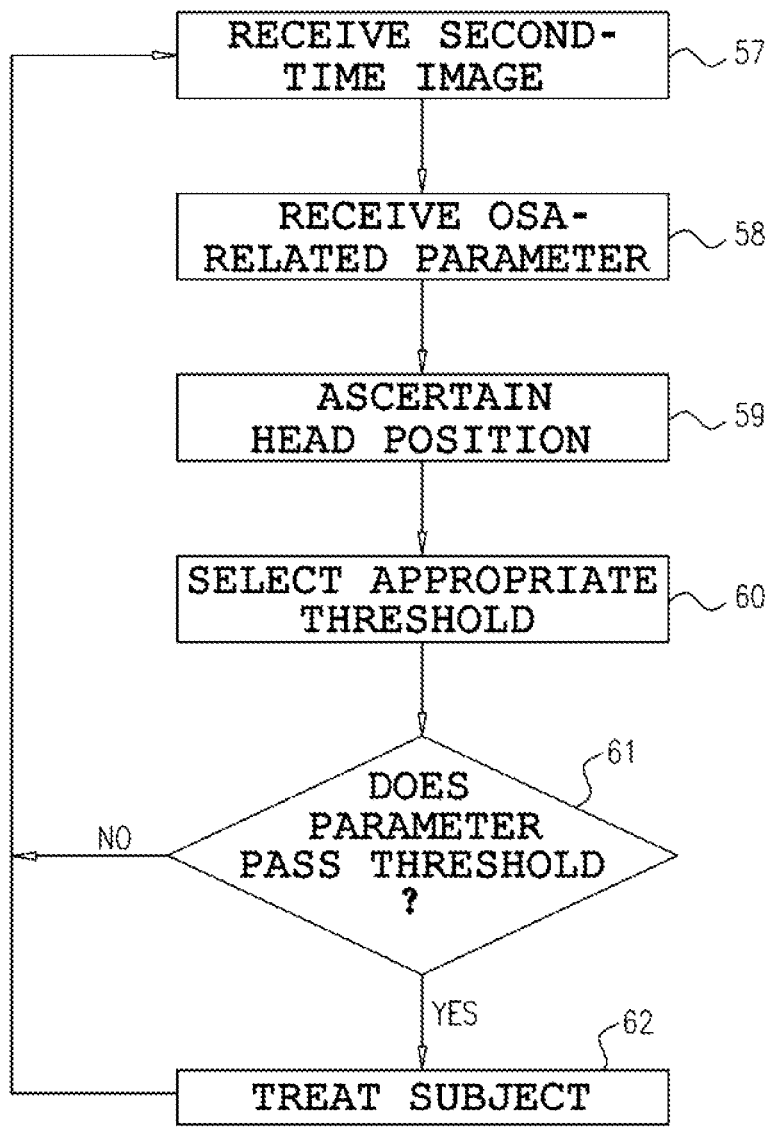
FIG. 3B shows a treatment-decision flowchart, in accordance with some applications of the present invention.

Reference is now made to FIG. 3B, which shows a treatment-decision flowchart, in accordance with some applications of the present invention. At a second time following the first time (i.e., following the establishing of the thresholds), the control unit receives a second-time image from imaging device 50, at an image-receiving step 57. The control unit also receives a second-time value of the OSA-related parameter, at a parameter-receiving step 58. At a head-position ascertaining step 59, the control unit ascertains the second position of the subject's head exhibited in the second-time image, e.g., as was done in head-position-ascertaining step 53 of FIG. 3A. (Step 59 may occur prior to step 58.) Then, at a threshold-selection step 60, the control unit selects the threshold that was established at the first time and corresponds to the ascertained head position. At a decision step 61, the control unit decides whether to treat the subject, by comparing the OSA-related parameter to the selected threshold. If the parameter passes the threshold, the subject is treated at a treatment step 62, the treatment being administered as described hereinabove with reference to FIG. 1. If the parameter does not pass the threshold, no treatment is administered. (Depending on the nature of the parameter, the parameter may "pass" the threshold in either direction. For example, a snore decibel level passes the threshold by exceeding the threshold, while a breathing volume passes the threshold by being less than the threshold.) This sequence of steps may then be repeated one or more times.

Typically, breathing sensor 28 senses the second-time value the OSA-related parameter sensing activity associated with breathing of the subject. The breathing sensor senses this activity, for example, by sensing airway pressure, snoring sounds, snoring motions, mechanical motion, and/or electrical activity.

In some applications, the treatment decision does not depend on the value of the OSA-related parameter, but rather, depends only on the position of the head. For example, if, during association-learning step 55, the control unit learns that the supine head position is strongly associated with OSA, the control unit may treat the subject every time the subject's head moves into a supine position regardless of any OSA-related parameters. (For other head positions, the control unit may base its decision on one or more OSA-related parameters, as discussed above.)

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for treating a subject for obstructive sleep apnea (OSA), the apparatus comprising:
   an implant, comprising:
     a wireless receiver;
     two or more electrodes; and
     circuitry coupled to the electrodes;
   an imaging device configured to generate images of the subject while the subject sleeps;
   at least one antenna; and
   a control unit configured to:
     at a first time, in response to a set of training images received from the imaging device:
       learn an association between a position of a head of the subject and OSA of the subject, and
       in response to the association, establish, for an OSA-related parameter, at least two distinct thresholds corresponding to respective different head positions, and
     at a second time following the first time, in response to a second-time position of the subject's head exhibited in a second-time image received from the imaging device:
       select, from the established thresholds, a threshold that corresponds to the second-time position of the subject's head, and
       when a second-time value of the OSA-related parameter passes the selected threshold, treat the subject for OSA by driving the antenna to transmit a signal to the wireless receiver, the wireless receiver being configured to receive the signal, and the circuitry being configured to drive the electrodes to apply current to an anatomical site of the subject in response to the received signal.

2. The apparatus according to claim 1, wherein the implant is configured to be implanted sublingually.

3. The apparatus according to claim 2, wherein the two or more electrodes are configured to be coupled to a sublingual muscle of the subject.

4. The apparatus according to claim 1, further comprising a breathing sensor configured to sense the second-time value of the OSA-related parameter by sensing activity associated with breathing of the subject.

5. The apparatus according to claim 4, wherein the breathing sensor is configured to sense activity associated with breathing of the subject by sensing a phenomenon selected from the group consisting of: airway pressure, snoring sounds, snoring motions, mechanical motion, and electrical activity.

6. A method for treating a subject for obstructive sleep apnea (OSA), the method comprising:
   using an imaging device, generating a set of training images of the subject while the subject sleeps;
   using a control unit:
      in response to the set of training images, learning an association between a position of a head of the subject and OSA of the subject; and
      in response to the association, establishing, for an OSA-related parameter, at least two distinct thresholds corresponding to respective different head positions;
   using the imaging device, generating a second-time image of the subject while the subject sleeps; and
   using the control unit, in response to a second-time position of the subject's head exhibited in the second-time image:
      selecting, from the established thresholds, a threshold that corresponds to the second-time position of the subject's head, and
      when a second-time value of the OSA-related parameter passes the selected threshold, treating the subject for OSA by driving an implant to apply current to an anatomical site of the subject.

7. The method according to claim 6,
   wherein the method is for use with at least one antenna,
   wherein the implant includes a wireless receiver, two or more electrodes, and circuitry coupled to the electrodes, and
   wherein treating the subject comprises:
      using the control unit to drive the antenna to transmit a signal to the wireless receiver; and
      using the circuitry, driving the electrodes to apply current to the anatomical site of the subject, in response to the signal.

8. The method according to claim 7, further comprising implanting the implant in the subject.

9. The method according to claim 8, wherein implanting the implant in the subject comprises sublingually implanting the implant.

10. The method according to claim 6, further comprising using a breathing sensor to sense the second-time value of the OSA-related parameter by sensing activity associated with breathing of the subject.

11. The method according to claim 10, wherein sensing activity associated with breathing of the subject comprises sensing activity associated with breathing of the subject by sensing a phenomenon selected from the group consisting of: airway pressure, snoring sounds, snoring motions, mechanical motion, and electrical activity.

12. Apparatus for treating a subject for obstructive sleep apnea (OSA), the apparatus comprising:
   an implant, comprising:
      a wireless receiver;
      two or more electrodes; and
      circuitry coupled to the electrodes;
   an imaging device configured to generate images of the subject while the subject sleeps;
   at least one antenna; and
   a control unit configured to:
      at a first time, in response to a set of training images received from the imaging device, learn an association between a position of a head of the subject and OSA of the subject, and
      at a second time following the first time, in response to (a) a second-time position of the subject's head exhibited in a second-time image received from the imaging device, and (b) the learned association, treat the subject for OSA by driving the antenna to transmit a signal to the wireless receiver, the wireless receiver being configured to receive the signal, and the circuitry being configured to drive the electrodes to apply current to an anatomical site of the subject in response to the received signal.

* * * * *